United States Patent [19]

Oberster et al.

[11] Patent Number: 5,137,976

[45] Date of Patent: Aug. 11, 1992

[54] ANHYDROUS METAL SALTS OF α,β-ETHYLENICALLY UNSATURATED CARBOXYLIC ACIDS AND RELATED METHODS

[75] Inventors: Arthur E. Oberster, North Canton; Takatsugu Hashimoto, Akron, both of Ohio

[73] Assignee: Bridgestone/Firestone, Inc., Akron, Ohio

[21] Appl. No.: 801,040

[22] Filed: Dec. 3, 1991

Related U.S. Application Data

[62] Division of Ser. No. 509,278, Apr. 16, 1990.

[51] Int. Cl.$^5$ ............... C08F 279/02; C08F 255/04; C08F 255/06; C08K 5/14

[52] U.S. Cl. ................... 525/274; 525/304; 525/313; 525/316; 525/319; 525/289; 525/292; 525/387; 524/534; 524/533; 524/536; 524/575; 524/575.5; 523/333

[58] Field of Search ............... 525/274, 304; 524/534, 524/536, 575, 575.5

[56] References Cited

U.S. PATENT DOCUMENTS

| | | | |
|---|---|---|---|
| 3,823,122 | 7/1974 | Schuh et al. | 260/85.1 |
| 4,056,269 | 11/1977 | Pollitt et al. | 273/218 |
| 4,065,537 | 12/1977 | Miller et al. | 264/143 |
| 4,082,288 | 4/1978 | Martin et al. | 273/218 |
| 4,141,559 | 2/1979 | Melvin et al. | 273/220 |
| 4,191,671 | 3/1980 | Kataoka et al. | 260/23.7 |
| 4,192,790 | 3/1980 | McKinstry et al. | 260/31.2 |
| 4,266,772 | 5/1981 | Martin et al. | 273/218 |
| 4,495,326 | 1/1985 | Donatelli et al. | 524/533 |
| 4,500,466 | 2/1985 | Hayes et al. | 260/429.9 |
| 4,529,770 | 7/1985 | Hayes et al. | 524/445 |
| 4,546,980 | 10/1985 | Gendreau et al. | 273/218 |
| 4,616,048 | 10/1986 | DeTrano et al. | 523/166 |
| 4,688,801 | 8/1987 | Reiter | 273/218 |
| 4,713,409 | 12/1987 | Hayes et al. | 524/518 |
| 4,715,607 | 12/1987 | Llort et al. | 273/218 |
| 4,720,526 | 1/1988 | Roland | 525/273 |
| 4,726,590 | 2/1988 | Molitor | 273/220 |
| 4,770,422 | 9/1988 | Isaac | 273/218 |
| 4,929,678 | 5/1990 | Hamada et al. | 525/193 |
| 4,955,613 | 9/1990 | Gendreau et al. | 273/218 |
| 4,971,329 | 11/1990 | Llort et al. | 273/218 |
| 4,974,852 | 12/1990 | Hiraoka et al. | 273/218 |
| 4,990,570 | 2/1991 | Saito et al. | 525/254 |

FOREIGN PATENT DOCUMENTS

63-223048 9/1988 Japan.

*Primary Examiner*—James J. Seidleck
*Assistant Examiner*—Vasu S. Jagannathan
*Attorney, Agent, or Firm*—Frank J. Troy, Sr.

[57] ABSTRACT

A reinforcing agent for vulcanizable rubber compounds comprises an anhydrous metal salt of an α,β-ethylenically unsaturated carboxylic acid having a crystalline structure consisting essentially of plates and fibers. Vulcanizable rubber compounds containing such reinforcing agents have improved physical properties over rubber compounds containing conventional metal carboxylic acid salts. Methods for the preparation of such anhydrous metal salts and methods for the reinforcement of vulcanizable rubber compounds therewith are also provided.

3 Claims, 3 Drawing Sheets

2.0 μ  5,000 X 2.0μ     5,000 X

ANHYDROUS METAL SALTS OF α,β-ETHYLENICALLY UNSATURATED CARBOXYLIC ACIDS AND RELATED METHODS

This application is a division of application Ser. No. 07/509,278 filed on Apr. 16, 1990.

TECHNICAL FIELD

The present invention provides a method for producing metal salts of α,β-ethylenically unsaturated carboxylic acids. Such metal salts have been added to rubber compositions heretofore in order to improve certain physical properties of the rubber such as tensile strength and modulus. The salts of the present invention are anhydrous and have a unique crystalline structure which has been found herein to produce improved properties in vulcanizable rubbers compounded therewith.

BACKGROUND OF THE INVENTION

The preparation of metal salts of various carboxylic acids such as methacrylic acid is described in several patents. U.S. Pat. No. 4,082,288, for instance, relates to the preparation of basic zinc methacrylate by milling under agitation methacrylic acid with a suspension of zinc oxide in a liquid medium such as water or a volatile organic liquid.

U.S. Pat. No. 4,100,182 relates to a method for preparing an adjuvant for an elastomeric composition which involves mixing methacrylic acid with zinc oxide in a liquid medium in the proportions required to form basic zinc methacrylate, removing the liquid medium and finely dividing the resulting reaction product. The reference teaches that the liquid medium may be water or a volatile organic liquid such as a hydrocarbon liquid or an alkanol.

In U.S. Pat. No. 4,500,466, owned by the Assignee of record herein, a method is provided for the preparation of zinc methacrylate powder involving the reaction of zinc oxide and methacrylic acid in a liquid aliphatic hydrocarbon such as hexane.

Despite the existence of metal salts of carboxylic acids and their widespread use in rubber polymer compounds the present invention provides a novel form of such salts and method for the preparation thereof. These salts provide superior physical properties in vulcanizable rubbers compounded therewith.

DISCLOSURE OF THE INVENTION

It is, therefore, an object of the present invention to provide a method for preparing anhydrous metal salts of α,β-ethylenically unsaturated carboxylic acids having a crystalline structure consisting essentially of plates and fibers.

It is another object of the present invention to provide a method for producing a reinforcing agent for vulcanizable rubber comprising metal salts of α,β-ethylenically unsaturated carboxylic acids having a crystalline structure consisting essentially of plates and fibers.

It is another object of the present invention to provide anhydrous metal salts of α,β-ethylenically unsaturated carboxylic acids, having a crystalline structure consisting essentially of plates and fibers, for addition to vulcanizable rubber polymers.

It is still another object of the present invention to provide a reinforcing agent for vulcanizable rubber comprising metal salts of α,β-ethylenically unsaturated carboxylic acids having a crystalline structure consisting essentially of plates and fibers.

It is still another object of the present invention to provide a method for reinforcing vulcanizable rubber.

It is yet another object of the present invention to provide cured rubber compounds, reinforced with metal salts of α,β-ethylenically unsaturated carboxylic acids, having a crystalline structure consisting essentially of plates and fibers, and having improved physical properties.

In general, a reinforcing agent for vulcanizable rubber compounds is provided which comprise an anhydrous metal salt of an α,β-ethylenically unsaturated carboxylic acid having a crystalline structure consisting essentially of plates and fibers.

The present invention also provides a method for the preparation of an anhydrous metal salt of an α,β-ethylenically unsaturated carboxylic acid having a crystalline structure consisting essentially of plates and fibers which comprises the steps of reacting an organometallic salt of a metal selected from the group consisting of zinc, iron (II), copper (II) and alkaline earth metals with an α,β-ethylenically unsaturated carboxylic acid having from 3 to about 30 carbon atoms in an organic hydrocarbon solvent with vigorous agitation, removing the solvent, and recovering the anhydrous metal salt.

A method for improving the physical properties in cured rubber compounds is also provided which comprises the steps of incorporating from about 5 to 100 parts by weight of an anhydrous metal salt of an α,β-ethylenically unsaturated carboxylic acid, having a crystalline structure consisting essentially of plates and fibers, into 100 parts of a vulcanizable rubber selected from the group consisting of natural rubber, synthetic rubber and blends thereof; and thereafter curing the rubber compound with a peroxide compound in a conventional manner.

The present invention also provides vulcanizable rubber compositions. These compositions comprise a vulcanizable rubber selected from the group consisting of natural rubber, synthetic rubber and mixtures thereof and from about 5 to 100 parts by weight of an anhydrous metal salt of an α,β-ethylenically unsaturated carboxylic acid, having a crystalline structure consisting essentially of plates and fibers, per 100 parts of the vulcanizable rubber.

These and other objects of the present invention together with the advantages thereof over existing metal salts, which shall become apparent from the specification which follows, are accomplished by the invention as hereinafter described and claimed.

PREFERRED EMBODIMENT FOR CARRYING OUT THE INVENTION

Figure 1:
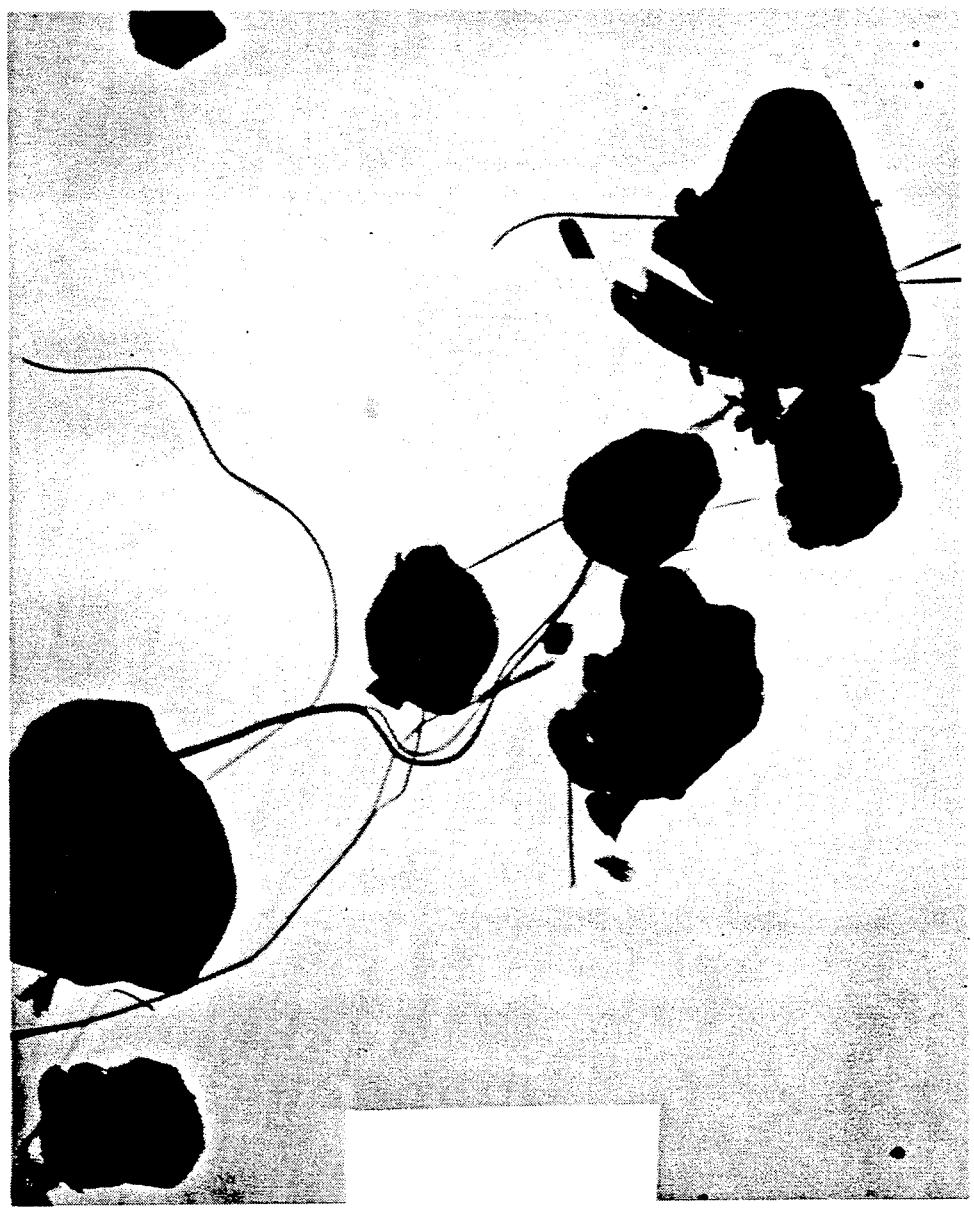
FIG. 1 is an electron photomicrograph of anhydrous zinc dimethacrylate at 5000× magnification prepared according to the present invention.

The subject of the present invention is the preparation of anhydrous zinc dimethacrylate which provides a crystalline structure consisting essentially of plates and some fibers, detected by transmission electron microscopy (TEM). Zinc dimethacrylate prepared in aqueous media is hydrated and provides a crystalline structure primarily of needles and powder. When prepared in an aliphatic hydrocarbon solvent, as described in U.S. Pat. No. 4,500,466, both crystalline structures are present. That is, the product comprises a mixture primarily of needles and powder (hydrated form) and some plates (anhydrous form). We have found that the plate structure imparts improved physical properties when incorporated into vulcanizable rubbery polymers as compared to when the needle and powder structure is selected or mixtures of both structures are selected. While the desired anhydrous form comprises a mixture of plates and fibers, the structure consists essentially of plates which are believed to be responsible for improving the physical properties of the rubber. As will be discussed hereinbelow, it is the physical properties of the cured rubber compound that are further improved.

Rubbers or rubbery polymers with which the anhydrous metal salts of the present invention having plate structure, can be employed include natural rubber, ethylene propylene rubber (EPR), ethylene propylene diene rubber (EPDM), nitrile rubber, neoprene, diene rubbers, copolymers of a conjugated diene and at least one monoolefin and blends thereof. The copolymers of conjugated dienes may be derived from conjugated dienes such as 1,3-butadiene, 2-methyl-1,3-butadiene(isoprene), 2,3-dimethyl-1,3-butadiene, 1,3-pentadiene, 1,3-hexadiene and the like, as well as mixtures of the foregoing dienes. The preferred conjugated diene is 1,3-butadiene.

The copolymers may be derived from various monoolefinic monomers including vinyl aromatic monomers such as styrene, alpha-methyl styrene, vinyl naphthalene, vinyl pyridine and the like; alkyl acrylates or methacrylates such as methyl acrylate, ethyl acrylate, butyl acrylate, methyl methacrylate, butyl methacrylate and the like; unsaturated nitriles such as acrylonitrile, methacrylonitrile and the like and vinyl halides such as vinyl chloride, vinylidene chloride and the like as well as mixtures of the foregoing monoolefins. The copolymers may contain up to 50 percent by weight of the monoolefin based upon the total weight of copolymer. The preferred copolymer is a copolymer of a conjugated diene, especially butadiene, and a vinyl aromatic hydrocarbon, especially styrene. Typical of styrene-butadiene rubbery copolymers which may be utilized is a styrene-butadiene copolymer having a bound styrene content of 23.5 percent, a viscosity (ML4 at 100° C.) of 50 and a specific gravity of 0.94 available under the designation S1502 from The Firestone Tire & Rubber Company.

The above-described copolymers of conjugated dienes and their method of preparation are well known in the rubber and polymer arts. Many of the polymers and copolymers are commercially available.

In general, the metal salts are derived from the reaction of a metal selected from the group consisting of zinc, iron (II) and copper (II) as well as alkaline earth metals such as magnesium and calcium and an $\alpha,\beta$-ethylenically unsaturated carboxylic acid having from about 3 to 30 carbon atoms, preferably acrylic acid or methacrylic acid. Particularly preferred is zinc dimethacrylate.

In order to obtain the anhydrous zinc dimethacrylate consisting essentially of plate, crystalline structure, an organic salt of zinc, or other metal for a metal carboxylate salt, is reacted with the $\alpha,\beta$-ethylenically unsaturated carboxylic acid in an organic hydrocarbon solvent. Particularly preferred are the aliphatics, such as hexane. The organic moiety of the metal salt is selected from the group consisting of aliphatics having from 1 to about 6 carbon atoms, with diethyl zinc being particularly preferred.

In the preparation of zinc dimethacrylate via the reaction of diethyl zinc and methacrylic acid, the by-product is ethane so an anhydrous product is obtained. Following the conventional preparation involving zinc oxide and methacrylic acid, the by-product is water and accordingly a product that is partially hydrated is obtained. The water produced can form a hydrate with the product and the hydrated form takes on a needle and powder type of crystalline structure with a minimum of the desirable plate structure. The hydrated product shows both needle and plate structures and is therefore a mixture of anhydrous and hydrated product.

As an example of the preparation of anhydrous zinc dimethacrylate, diethyl zinc is reacted with methacrylic acid in an amount of from about 0.5 to about 0.6 moles of diethyl zinc per mole of methacrylic acid in a volatile organic liquid hydrocarbon.

While not essential, it is generally preferred to include a small amount of a nonionic surfactant in the dispersion medium as this aids in producing a fluid suspension which is pumpable and pourable. Various well known nonionic surfactants can be utilized for that purpose including silicone type surfactants and alkylaryl polyether alcohol types. Preferred nonionic surfactants are the alkylaryl polyether alcohols.

Amounts of nonionic surfactant included in the dispersion medium may range from about 0.1 to about 1.0 percent, preferably 0.3 to 0.5 percent by weight based on the combined weight of zinc oxide and methacrylic acid.

The reaction is preferably conducted at room or ambient temperatures, i.e., no added heat, under agitation and in the presence of the nonionic surfactant. This reaction procedure produces a fluid suspension which as indicated above is both pumpable and pourable. If desired, the reaction can be conducted at temperatures of up to about 70° C. and without a surfactant. In this latter case, a slurry or thick paste is obtained which does not pour well. While this procedure is not preferred, it does not appear to degrade the finished product.

Reaction times may vary considerably depending on factors such as batch size, degree of agitation and the like. In general, reaction times may range from about 4 to about 20 hours or more.

In the preferred embodiment, as the reaction nears completion, the product takes on the form of a fluid suspension of zinc dimethacrylate particles in the liquid medium, whereas when the reaction is conducted at higher temperatures and without surfactant, the product takes on the form of a slurry of zinc dimethacrylate particles in the liquid medium.

In any event, the next step is to recover the particles of zinc dimethacrylate from the liquid medium. This can be accomplished by any convenient method. Thus, for example, the zinc dimethacrylate particles may be recovered by filtration (which is preferred) or by removal of the liquid medium as by evaporation. When the zinc dimethacrylate particles are recovered by filtration, it is often desirable and preferred to remove additional portions of the liquid medium by pressing the particles.

Following the recovery step, the zinc dimethacrylate particles are dried to produce the zinc dimethacrylate powder. Drying can be accomplished by any conventional method. Thus, air drying and/or vacuum drying can be utilized. It is often preferred to first air dry the particles and then vacuum dry in an oven at temperatures of from about 60° C. to about 70° C.

The amount of the metal salt of the present invention that can be added to the rubber ranges generally from about 5 to 100 parts by weight, per 100 parts of rubber (phr), depending somewhat upon which of the foregoing types of salt is selected.

The metal salts of the present invention can be added to the rubber during compounding by general compounding techniques, such as dry mixing, or other known to those skilled in the art. Alternatively, it can be added as a suspension in an organic solvent to a polymer cement, formed by preparing the desired polymer in an organic solvent. Such a process is described in greater detail in copending application, U.S. Ser. No. 509,277 now U.S. Pat. No. 5,096,943.

The polymer compounds containing the metal salts of the present invention are cured with peroxides. Peroxide curing agents which may be used in the compositions include organic peroxides such as dicumyl peroxide, bis-(t-butyl peroxy(diisopropyl benzene, t-butyl perbenzoate, di-t-butyl peroxide, 2,5-dimethyl-2,5-di-t-butyl peroxide-hexane and the like. The preferred peroxide curing agents are bis-(t-butyl peroxy)-diisopropyl benzene and dicumyl peroxide.

Amounts of peroxide curing agents included in the compositions will depend upon the type rubber utilized and may broadly be stated as cure effective amounts. In general, such amounts may range from about 0.2 to about 10 parts by weight per 100 parts by weight of rubbery polymer.

The compositions may optionally contain other additives commonly utilized in rubber compositions such as process and extender oils, antioxidants, waxes and the like. Additionally, fillers or mixtures of fillers can be used in amounts of from about 30 to about 70 parts by weight per 100 parts by weight of rubbery polymer.

In order to demonstrate practice of the present invention, an emulsion SBR (S1502 described hereinabove) was selected and compounded with four different forms of zinc dimethacrylate. Compound No. 1 contained anhydrous zinc dimethacrylate of the present invention. Compounds No. 2–4, were controls and contained a known zinc dimethacrylate, prepared according to U.S. Pat. No. 4,500,466 and containing both plate and needle crystalline structure. The salts were prepared by reacting zinc oxide and methacrylic acid in hexane and in the presence of a surfactant. A molar ratio of zinc oxide to methacrylic acid of 0.5:1 was employed. The anhydrous zinc dimethacrylate employed in Compound No. 1 was that prepared by the method of this invention. Compounds No. 2, 3 and 4 feature salts prepared by the method of U.S. Pat. No. 4,500,466. Compound No. 2 featured the salt after 15 months of shelf storage, Compound No. 3 was after 8 months shelf storage and Compound No. 4 was after one month shelf storage.

The reaction products were separated and the solvent was removed after which the slurry was dried in an vacuum oven at room temperature to 150° C. The products were examined by TEM and found to contain both plate and needle structures. Also, by TGA and DSC analysis, the hydrous and anhydrous structure of the products was confirmed.

Each compound contained the surfactant tris nonpylphenyl phosphite and the curative Vulcup 40KE. The compositions of each compound and cured physical properties thereof are presented in Tables I and II, respectively. The rubber compounds were each cured for 40 minutes at 160° C.

TABLE I

| Zinc Dimethacrylate Reinforced Rubber Compounds | | | | |
|---|---|---|---|---|
| Compound | No. 1 | No. 2 | No. 3 | No. 4 |
| SBR | 100 | 100 | 100 | 100 |
| Zn(MA)$_2$$^a$ | 40 | | | |
| Zn(MA)$_2$$^b$ | | 40 | | |
| Zn(MA)$_2$$^b$ | | | 40 | |
| Zn(MA)$_2$$^b$ | | | | 40 |
| Antioxidant | 2 | 2 | 2 | 2 |
| Curative | 0.8 | 0.8 | 0.8 | 0.8 |

$^a$anhydrous zinc dimethacrylate
$^b$anhydrous and hydrated zinc dimethacrylate

TABLE II

| Physical Properties of Compounds No. 1 to 4 | | | | |
|---|---|---|---|---|
| Compound | No. 1 | No. 2 | No. 3 | No. 4 |
| 50% Modulus (psi) | 660 | 375 | 495 | 630 |
| 100% Modulus (psi) | 1275 | 810 | 1005 | 1095 |
| 200% Modulus (psi) | 2540 | 1650 | 2010 | 2135 |
| Tensile (psi) | 3015 | 2020 | 2455 | 2725 |
| Elongation (%) | 215 | 255 | 285 | 295 |

As can be seen from the data in Table II, the modulus and tensile values for Compound No. 1 which contained the anhydrous salt were noticeably higher than Compounds No. 2, 3 and 4 which contained varying amounts of both the anhydrous and hydrated salt.

Figure 2:
FIG. 2 is a electron photomicrograph of zinc dimethacrylate prepared in a conventional manner, after shelf-storage of 15 months utilizing an aliphatic hydrocarbon solvent.

As an example of the anhydrous and hydrated forms, reference should be made to FIGS. 1 and 2. The crystalline structure of FIG. 1, the salt featured Compound No. 1 consists essentially of plates with a few fibers running therebetween, and is characteristic of the anhydrous form of zinc dimethacrylate as well as other anhydrous metal salts of the present invention. Similarly, the crystalline structure of the conventional, hydrated form of zinc dimethacrylate is depicted in FIG. 2, the salt featured in Compound No. 2 which provides a mixture, largely comprising needles and powder with a single plate at the left of the photomicrograph.

Figure 3:
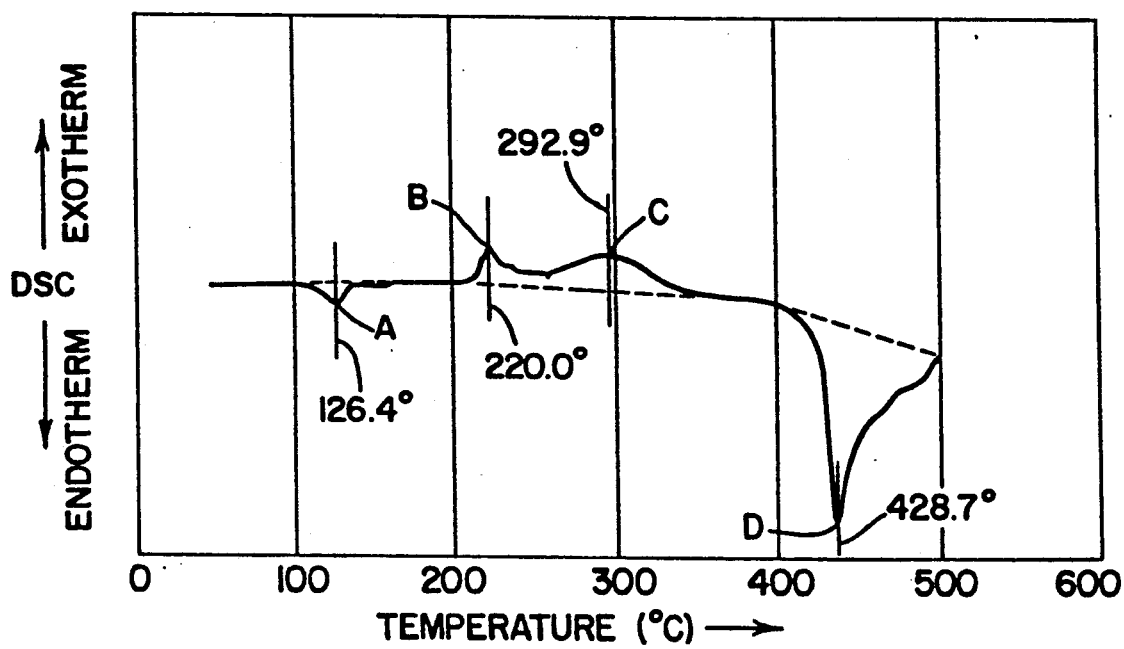
FIG. 3 is a graph depicting the curve resulting analysis by DSC of the anhydrous zinc dimethacrylate prepared according to the present invention.
Figure 4:
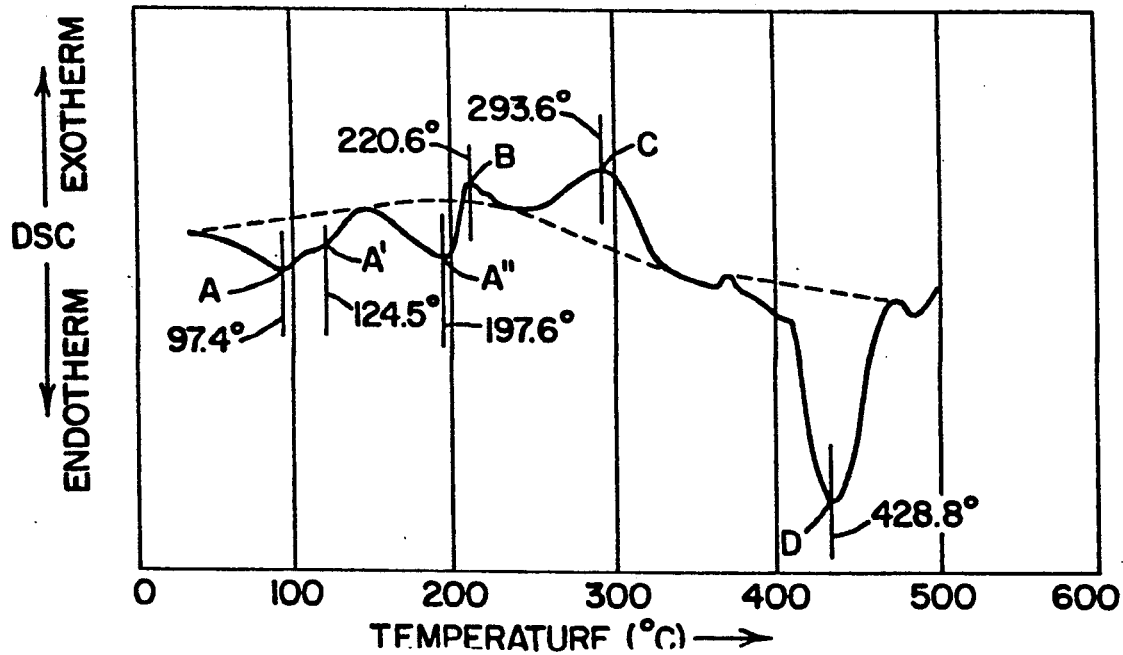
FIG. 4 is a graph depicting the curve resulting from analysis by DSC of zinc dimethacrylate prepared conventionally.

The analysis of both anhydrous and hydrated zinc dimethacrylate salts by DSC is depicted in FIGS. 3 and 4. In FIG. 3 depicting the salt featured in Compound No. 1, four transition points A–D were noted. Point A, an endotherm, represents the removal of a small quantity of water. Although the zinc dimethacylate was anhydrous, the salt is hygroscopic and hence, will pick up trace amounts of moisture from the atmosphere. Points B and C were both exothermic and represent the breakdown and removal of a small amount of methacrylic acid (B) and polymerization of the zinc dimethacrylate (C). Point D, another endotherm represented final degradation of the salt.

In FIG. 4 depicting the salt featured in Compound No. 2, transition points A, A' and A" are endotherms and represent removal of water. In a hydrated species, the water is held somewhat more tightly in the complex, therefore, the endotherms occur at higher temperature. Thus, A may represent removal of uncomplexed water, A' represents a loosely held complex of water, and A" represents a tightly bound complex of water. Transition point B is exothermic and represents breakdown of zinc dimethacrylate with subsequent removal of methacrylic acid. Points C and D again represented the polymerization exotherm (C) and salt degradation (D).

Next, in order to determine whether anhydrous salts could be hydrated and converted to needle and powder crystalline form and also if removal of the water of hydration from the hydrated salt would result in conversion of the needle and powder structure to the plate structure of the present invention, four additional compounds, No. 5–8 were prepared employing the emulsion SBR (S1502 described hereinabove). Each compound contained a different zinc dimethacrylate salt, described hereinbelow, an antioxidant and peroxide curative. Compositions, cure conditions and cured physical properties are presented in Tables III and IV, respectively.

Compound No. 5 contained anhydrous zinc dimethacrylate, prepared according to the present invention. Compound No. 6 contained hydrated zinc dimethacrylate, prepared according to U.S. Pat. No. 4,500,466 and shelf aged for 15 months. Compound No. 7 contained anhydrous zinc dimethacrylate that had been hydrated by exposure to two moles of water per mole of anhydrous zinc dimethacrylate. Compound No. 8 contained hydrated zinc dimethacrylate, prepared according to U.S. Pat. No. 4,500,466 and shelf aged for 15 months (the salt featured in Compound No. 6 after aging), which was heated at 150° C. for 30 minutes to remove as much water of hydration as possible.

TABLE III

| Zinc Dimethacrylate Reinforced Rubber Compounds | | | | |
|---|---|---|---|---|
| Compound | No. 5 | No. 6 | No. 7 | No. 8 |
| SBR | 100 | 100 | 100 | 100 |
| Zn(MA)$_2$$^a$ | 40 | | | |
| Zn(MA)$_2$$^b$ | | 40 | | |
| Zn(MA)$_2$$^c$ | | | 40 | |
| Zn(MA)$_2$$^d$ | | | | 40 |
| Antioxidant | 2 | 2 | 2 | 2 |
| Peroxide | 0.8 | 0.8 | 0.8 | 0.8 |

$^a$Anhydrous zinc dimethacrylate
$^b$Hydrated zinc dimethacrylate
$^c$Anhydrous zinc dimethacrylate (+H$_2$O)
$^d$Hydrated zinc dimethacrylate (−H$_2$O)

TABLE IV

| Cured Physical Properties of Compounds No. 5 to 8 | | | | |
|---|---|---|---|---|
| Compound | No. 5 | No. 6 | No. 7 | No. 8 |
| Cured 20 min. at 160° C. | | | | |
| 50% Modulus (psi) | 475 | 260 | 285 | 210 |
| 100% Modulus (psi) | 930 | 530 | 555 | 370 |
| 200% Modulus (psi) | 1925 | 1110 | 1185 | 725 |
| 300% Modulus (psi) | — | — | — | 1015 |
| Tensile (psi) | 2655 | 1670 | 1470 | 1535 |
| Elongation (%) | 265 | 310 | 240 | 480 |
| Cured 40 min. at 160° C. | | | | |
| 50% Modulus (psi) | 660 | 375 | 355 | 290 |
| 100% Modulus (psi) | 1275 | 810 | 750 | 535 |
| 200% Modulus (psi) | 2540 | 1615 | — | 1015 |
| 300% Modulus (psi) | — | — | — | 1395 |
| Tensile (psi) | 3015 | 2020 | 1300 | 1605 |
| Elongation (%) | 215 | 255 | 165 | 355 |

From the data reported in Table II, it is immediately apparent that Compound No. 5, containing anhydrous zinc dimethacrylate, possessed the superior physical properties as compared to the other three compounds. By comparing Compounds 6–8 it is also apparent that the removal of water from the hydrated salt did not yield as good a results for Compound No. 8 as for the anhydrous salt employed in Compound No. 5; hence, removal of water did not provide the desirable plate structure. However, the addition of water to the anhydrous metal salt of the present invention did show a reduction in the physical properties possessed by Compound No. 7, indicating that the desirable plate structure was decreased. Thus, the preferred form of metal salt is anhydrous, having a crystalline structure consisting essentially of plates and fibers.

In conclusion, it should be clear from the foregoing examples and specification disclosure that the addition of anhydrous metal salts of α,β-ethylenically unsaturated carboxylic acids to rubbery polymers improves the physical properties of the rubber compound as compared to rubber compounds to which conventional, hydrated salts have been added. It is to be understood that the invention is not limited to the anhydrous zinc dimethacrylate and SBR exemplified herein or by the disclosure of other metal salts and typical rubber polymers provided herein, the examples having been provided merely to demonstrate practice of the subject invention. Those skilled in the art may readily select other anhydrous metal salts and/or rubbery polymers, according to the disclosure made hereinabove.

Thus, it is believed that any of the variables disclosed herein can readily be determined and controlled without departing from the scope of the invention herein disclosed and described. Moreover, the scope of the invention shall include all modifications and variations that fall within the scope of the attached claims.

We claim:

1. A method for improving the physical properties in cured rubber compounds comprising the steps of:
    incorporating from about 5 to 100 parts by weight of an anhydrous metal salt of an α,β-ethylenically unsaturated carboxylic acid, having a crystalline structure consisting essentially of plates and fibers, into 100 parts of vulcanizable rubber selected from the group consisting of natural rubber, synthetic rubber and blends thereof; and
    thereafter curing said rubber compound with a peroxide compound in a conventional manner.

2. A method, as set forth in claim 1, wherein said metal salt is selected from the group consisting of zinc, iron (II), copper (II) and the alkaline earth metals and said α,β-ethylenically unsaturated carboxylic acid has from 3 to about 40 carbon atoms.

3. A method, as set forth in claim 2, wherein said metal salt is zinc dimethacrylate.

* * * * *

UNITED STATES PATENT AND TRADEMARK OFFICE
CERTIFICATE OF CORRECTION

PATENT NO. : 5,137,976
DATED : August 11, 1992
INVENTOR(S) : Oberster et al.

It is certified that error appears in the above-identified patent and that said Letters Patent is hereby corrected as shown below:

On the title page
[73] Assignee:     Bridgestone/Firestone, Inc., Akron, Ohio should read:

[73] Assignee:     Bridgestone/Firestone, Inc., Akron, Ohio
                   Bridgestone Corporation, Tokyo, Japan Signed and Sealed this Thirteenth Day of February, 1996

Attest:

BRUCE LEHMAN

*Attesting Officer*     Commissioner of Patents and Trademarks